United States Patent
Veldman

(10) Patent No.: US 9,265,641 B2
(45) Date of Patent: Feb. 23, 2016

(54) METHOD AND APPARATUS FOR DISCOURAGING W-SITTING

(71) Applicant: Bernie T. Veldman, Granger, IN (US)

(72) Inventor: Bernie T. Veldman, Granger, IN (US)

( * ) Notice: Subject to any disclaimer, the term of this patent is extended or adjusted under 35 U.S.C. 154(b) by 0 days.

(21) Appl. No.: 13/836,956

(22) Filed: Mar. 15, 2013

(65) Prior Publication Data

US 2013/0211299 A1 Aug. 15, 2013

Related U.S. Application Data

(63) Continuation-in-part of application No. 13/616,011, filed on Sep. 14, 2012.

(60) Provisional application No. 61/535,449, filed on Sep. 16, 2011.

(51) Int. Cl.
| | |
|---|---|
| *G08B 23/00* | (2006.01) |
| *A61F 5/01* | (2006.01) |
| *A61B 5/00* | (2006.01) |
| *A61B 5/11* | (2006.01) |

(52) U.S. Cl.
CPC .................. *A61F 5/01* (2013.01); *A61B 5/1116* (2013.01); *A61B 5/1126* (2013.01); *A61B 5/6804* (2013.01); *A61B 5/6828* (2013.01); *A61B 5/0024* (2013.01); *A61B 5/6831* (2013.01); *A61B 5/742* (2013.01); *A61B 5/7405* (2013.01); *A61B 5/7455* (2013.01); *A61B 2503/06* (2013.01); *A61B 2562/0247* (2013.01)

(58) Field of Classification Search
USPC ............................................ 340/573.1, 573.7
See application file for complete search history.

(56) References Cited

U.S. PATENT DOCUMENTS

| | | | |
|---|---|---|---|
| 3,608,541 A | 9/1971 | Hall | |
| 3,644,919 A | 2/1972 | Mathauser | |
| 4,007,733 A | 2/1977 | Celeste et al. | |
| 4,703,625 A | 11/1987 | Caldwell | |
| 4,860,364 A * | 8/1989 | Giannini | 381/333 |
| 4,972,177 A * | 11/1990 | Nolan | 340/573.7 |
| 5,038,761 A | 8/1991 | Richardson | |
| 5,081,447 A | 1/1992 | Echols | |
| 5,398,697 A | 3/1995 | Spielman | |
| 5,469,861 A | 11/1995 | Piscopo et al. | |
| 5,592,689 A | 1/1997 | Matthews | |
| 5,643,329 A | 7/1997 | Solomonow et al. | |
| 5,782,790 A | 7/1998 | Allen | |
| 5,941,836 A | 8/1999 | Friedman | |

(Continued)

FOREIGN PATENT DOCUMENTS

| | | |
|---|---|---|
| DE | 3839494 A1 | 5/1990 |
| WO | 2009112281 A1 | 9/2009 |

OTHER PUBLICATIONS

European Patent Office, International Search Report, Nov. 30, 2012, 5 pages.

(Continued)

*Primary Examiner* — Brian Zimmerman
*Assistant Examiner* — Thomas McCormack
(74) *Attorney, Agent, or Firm* — Barnes & Thornburg LLP

(57) ABSTRACT

An orthotic apparatus includes a garment, first and second switches, a power source, an indicator and a series of electrical conductors. When a patient wearing the garment assumes an undesirable position, the switches are activated and the indicator produces an audible, visual or other prompt to remind the patient to change position.

17 Claims, 10 Drawing Sheets

(56) References Cited

U.S. PATENT DOCUMENTS

| | | |
|---|---|---|
| 6,019,738 A | 2/2000 | Brandon |
| 6,086,551 A | 7/2000 | Allen |
| 6,119,516 A | 9/2000 | Hock |
| 6,648,838 B1 | 11/2003 | Brandon et al. |
| 6,827,694 B2 | 12/2004 | Gladoun |
| 7,733,233 B2 | 6/2010 | O'Shea et al. |
| 7,878,055 B2 | 2/2011 | Balzano |
| 7,992,217 B2 | 8/2011 | Hyde et al. |
| 8,018,346 B2 | 9/2011 | Gottlieb et al. |
| 8,083,693 B1 | 12/2011 | McKeon et al. |
| 8,217,797 B2 | 7/2012 | Ikoyan |
| 2005/0237209 A1 | 10/2005 | Van Dongen |
| 2008/0094226 A1 | 4/2008 | O'Shea et al. |
| 2010/0109880 A1 | 5/2010 | Lee et al. |

OTHER PUBLICATIONS

European Patent Office, Written Opinion of the International Searching Authority, Nov. 30, 2012, 7 pages.

Banglab, "Perfect Posture", Internet, Dec. 12, 2009, pp. 1-4, http://bang.calit2.net/wiki/Perfect_Posture.

Inventables, "Conductive Elastic Fabric", Aug. 22, 2011, 1 page, http://www.inventables.com/technologies/conductive-elastic-fabric.

SPIO: Stabilizing Pressure Input Orthosis, "Short Pants", Aug. 22, 2011, 1 page, https://www.spioworks.org/page/aspx?nid=38&ion=products&pid=10.

* cited by examiner

METHOD AND APPARATUS FOR DISCOURAGING W-SITTING

The present invention generally relates to orthotic devices and, in particular, to a method and apparatus for discouraging W-sitting.

BACKGROUND AND SUMMARY OF TIME INVENTION

Figure 1:
FIG. 1 is a perspective view of a child in a W-sitting position.

FIG. 1 is a perspective view of a child in a W-sitting position. In this position, the medial aspect of both knees contacts the ground and the child's lower legs and feet extend outwardly and away from the knees. W-sitting can cause various short term and long term effects on a child's hips, knees, ankles and gait.

An orthotic apparatus may include a garment, a first switch having a first portion and a second portion connected to the garment, a second switch having a first portion and a second portion connected to the garment, a power source connected to the garment, an indicator connected to the garment, a first electrical conductor electrically coupled to the first portion of the first switch and the power source, a second electrical conductor electrically coupled to the power source and the indicator, a third electrical conductor electrically coupled to the indicator and the first portion of the second switch and a fourth electrical conductor electrically coupled to the second portion of the first switch and the second portion of the second switch.

In some embodiments of the invention, the indicator is activated when the first portion of the first switch contacts the second portion of the first switch and the first portion of the second switch simultaneously contacts the second portion of the second switch.

In other embodiments of the invention, the second portion of the first switch and the second portion of the second switch are integrally formed with the garment.

DETAILED DESCRIPTION OF THE EMBODIMENTS OF THE INVENTION

Figure 2:
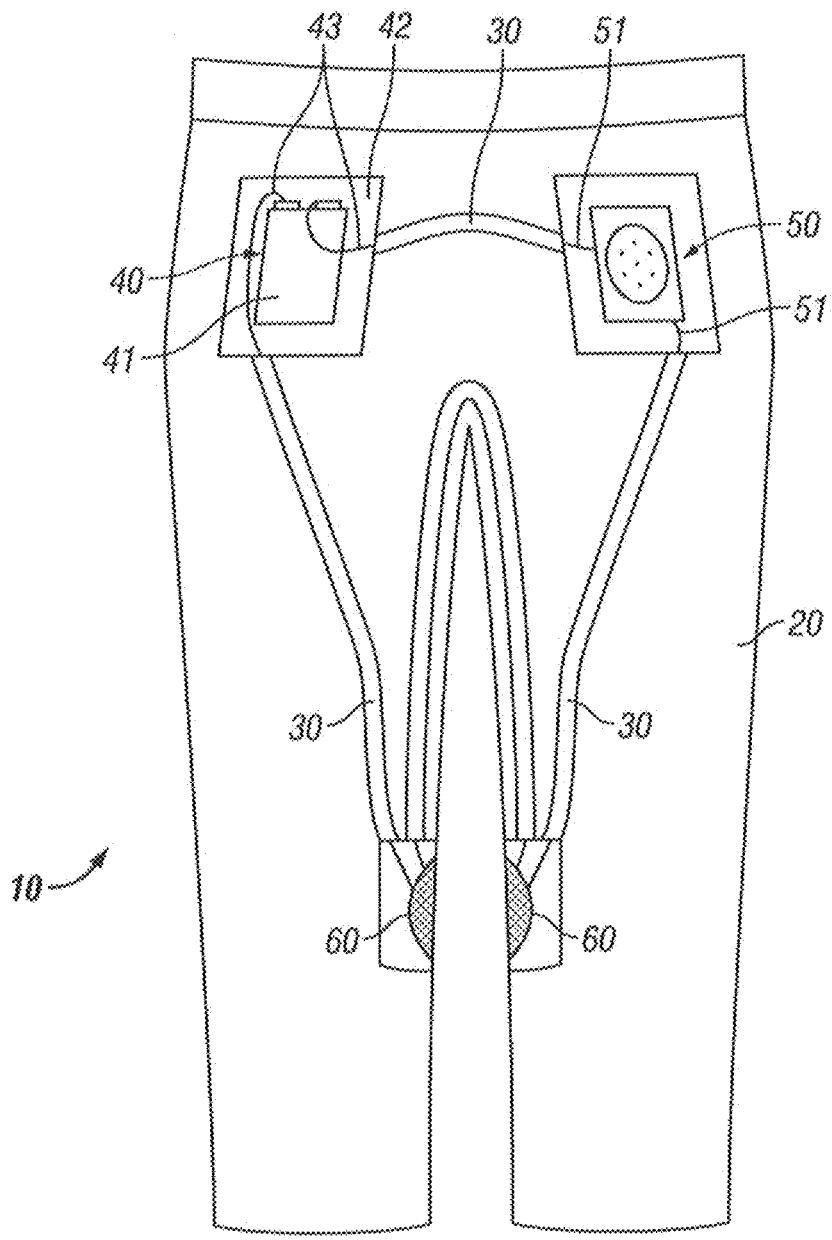
FIG. 2 is a rear plan view of an apparatus for discouraging W-sitting according to one embodiment of the present invention.

FIG. 2 is a rear plan view of an orthotic device, namely, apparatus 10 for discouraging W-sitting, according to one embodiment of the present invention. Apparatus 10 generally includes a garment 20, a plurality of electrical conductors 30, a power source 40, an indicator 50 and switches 60.

In the embodiment shown, garment 20 is a pair of pants that extend at least below the child's knees. The pants are preferably made from a heavy duty stretchable material such as Lycra® or spandex and are sized to fit snugly so as to avoid any slippage or rotational movement of the pants that would move the switches out of the desired position relative to the patient's knees.

In the embodiment shown, electrical conductors 30 are preferably a stretchable, conductive fabric stitched to the pants to create a circuit between power source 40, indicator 50, and switches 60, as described in greater detail below. The conductive fabric acts like wiring. In one embodiment, the conductive fabric is a silver plated (92%) nylon (8%) fabric that stretches in at least two directions. Conductive fabrics having other characteristics can also be used, so long as they can carry the needed electrical load and are sufficiently flexible.

In the embodiment shown, power source 40 is a standard 9V battery 41 positioned in a battery holder 42. Wires 43 from battery holder 42 are connected to two conductors 30 as shown by stitching or other means. Battery 41 can be replaced by triple A or other batteries. Other means of powering apparatus 10 can also be utilized.

In the embodiment shown, indicator 50 is a small buzzer, such as a piezo buzzer, or a tone generator. Wires 51 from indicator 50 are connected to two conductors 30 as shown by stitching or other means.

Two switches 60 are secured to garment 20 on the medial aspect of each knee so that when a patient W-sits the switches make contact with the floor. Switches 60 can be secured to garment 20 in various manners. In one embodiment of the invention, switches 60 are secured to garment 20 with hook and loop type fastener so that the position of switches 60 can be adjusted as desired. In one embodiment of the invention, switches 60 are flat, thin pressure sensors or membrane type switches. Wires 61 from switches 60 are connected to two conductors 30 as shown by stitching or other means.

As shown in FIG. 2, power source 40, indicator 50 and switches 60 are connected in series via conductors 30, and wires 41, 51 and 61. When a patient W-sits, both switches 60 make contact with the floor and close, thereby completing the circuit and activating indicator 50 to buzz or emit a tone. The buzzing or tone reminds the parents or other care giver to instruct the patient to change position. It also reminds the patient to change position.

Figure 3:
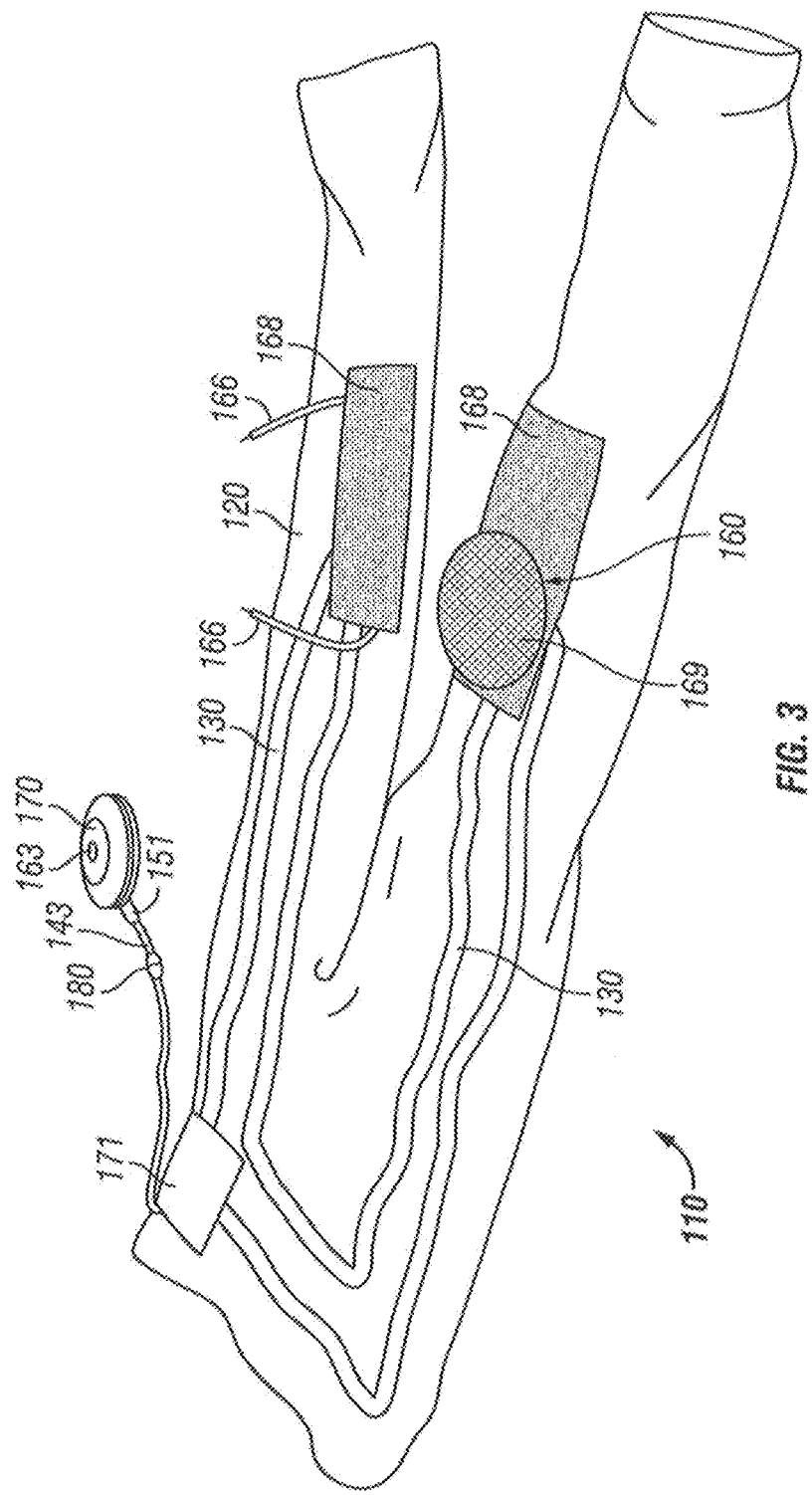
FIG. 3 is a perspective view of another embodiment of an apparatus for discouraging W-sitting according to another embodiment of the present invention.

FIG. 3 is a perspective view of an apparatus for discouraging W-sitting according to another embodiment of the present invention, in which elements corresponding to those shown in the prior embodiment are indicated by corresponding numbers preceded by the numeral "1." In this embodiment, the power source 140 and indicator 150 (not shown) are encased in a waterproof housing 170. The wire extending between power source 140 and indicator 150 is likewise encased in waterproof housing 170. One wire 151 from indicator 160 and one wire 143 from power source 140 extend from housing 170 and are coupled to the remainder of the circuit by a connector 180. These wires and housing 170 may be tucked into a pouch or pocket 171 on the garment 120.

Housing 170 can be made from any one of a number of waterproof materials, such as plastic. In one embodiment, housing 170 is permanently molded around power source 140 and indicator 150. In another embodiment, housing 170 is in the form of a case that can be opened to access power source 140 and indicator 150.

Figure 4:
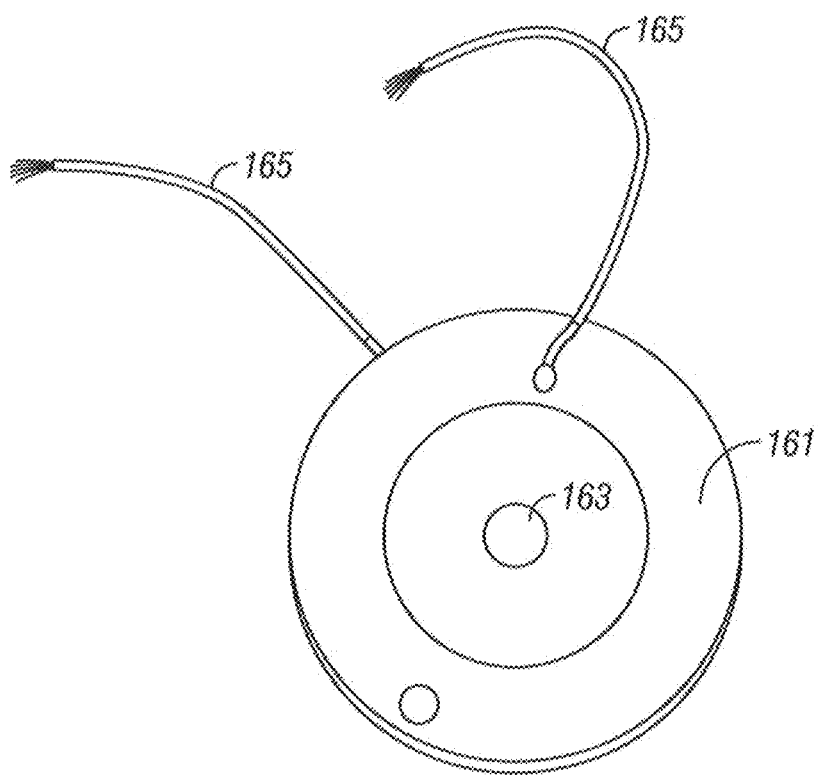
FIG. 4 is a top plan view of a switch that is a component of the apparatus shown in FIG. 3.
Figure 5:
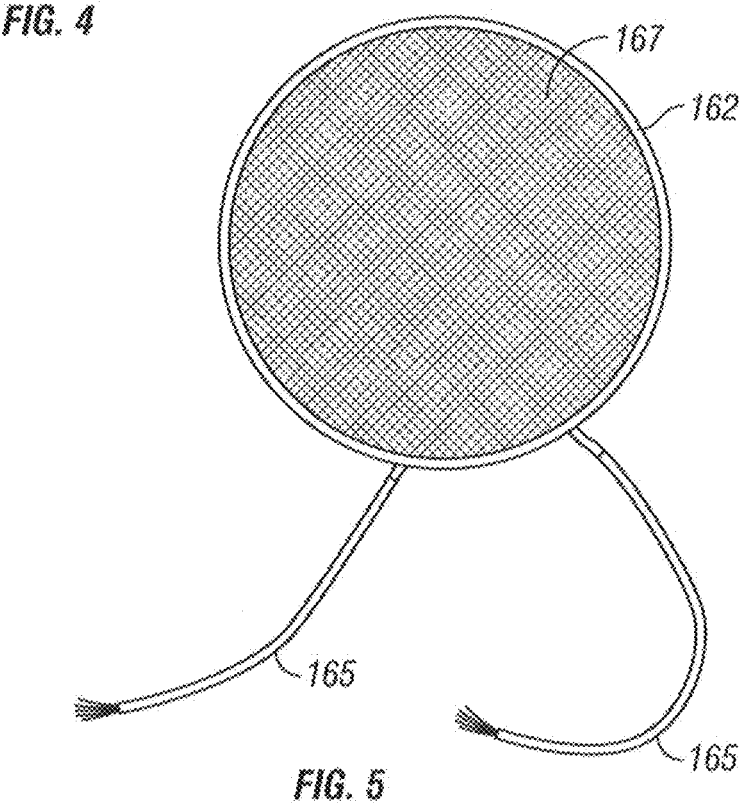
FIG. 5 is a bottom plan view of the switch shown in FIG. 4.
Figure 6:
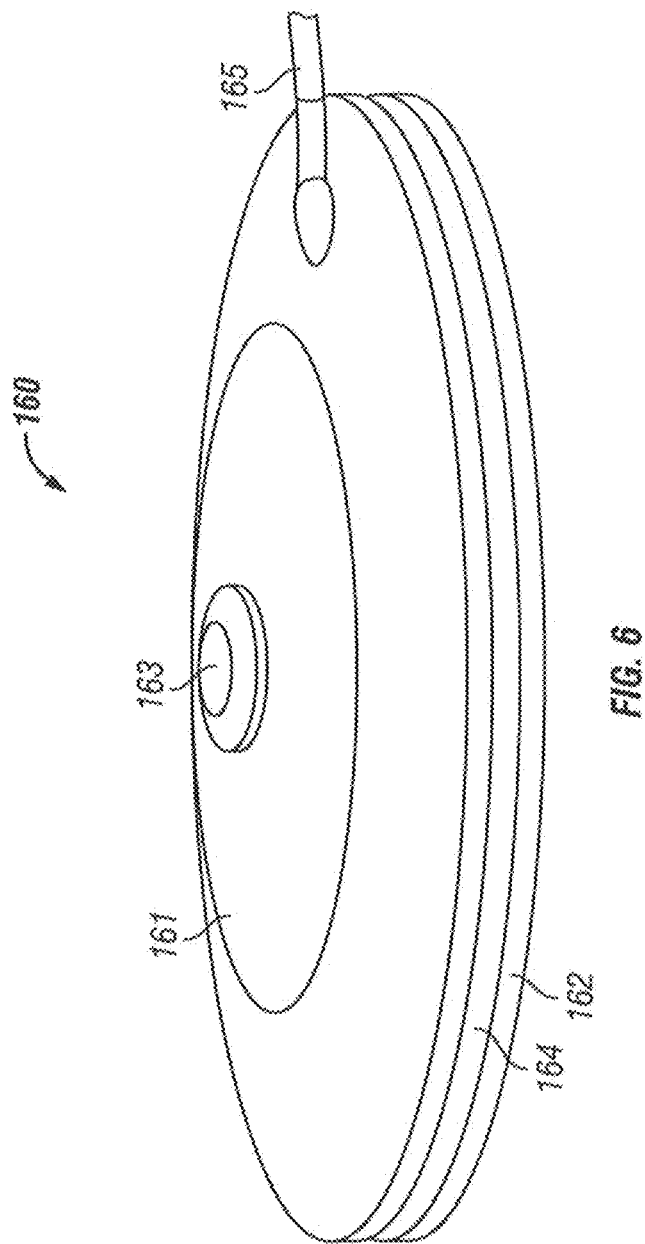
FIG. 6 is a perspective view of the switch shown in FIG. 4.

As shown in FIGS. 4-6, switch 160 in the embodiment shown is a pivot type switch including a first or upper plate 161, a second or lower plate 162 and a pivot point or post 163. In the un-activated state, an air gap 164 separates first plate 161 and second plate 162. A pair of wires 165 extend from and are electrically connected to first plate 161 and second plate 162, respectively. Wires 165 are in turn connected to wires 166 that are in electrical connection with conductors 130 on garment 120.

In the embodiment shown, hook members 167 of a hook and loop type fastening system are applied to second plate 162 of switch 160. Sections of the loop material portion 168 of the hook and loop type fastening system are secured to garment 120. Hook members 167 engage with loop material 168 to secure stitches 160 to garment 120. In this manner, switches 160 can be placed at the desired location for treatment of individual patients having different physical characteristics and W-sitting tendencies. In the embodiment shown, switches 160 further include a cloth covering 169 (not shown in FIGS. 4-6).

Although as noted above various types of switches can be used it may be desirable to utilize a switch that will activate the indicator as soon as both of the garment patient's knee begins to contact the ground, thereby activating the indicator before the patient is fully in the undesirable W-sitting position. Pivot switches 160 function in this manner. Switches other than the particular pivot switches shown could also be utilized to achieve the same result.

Figure 7:
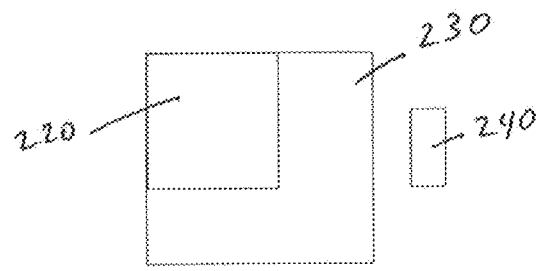
FIG. 7 is a schematic view of another embodiment of an apparatus for discouraging W-sitting according to another embodiment of the present invention.
Figure 7:
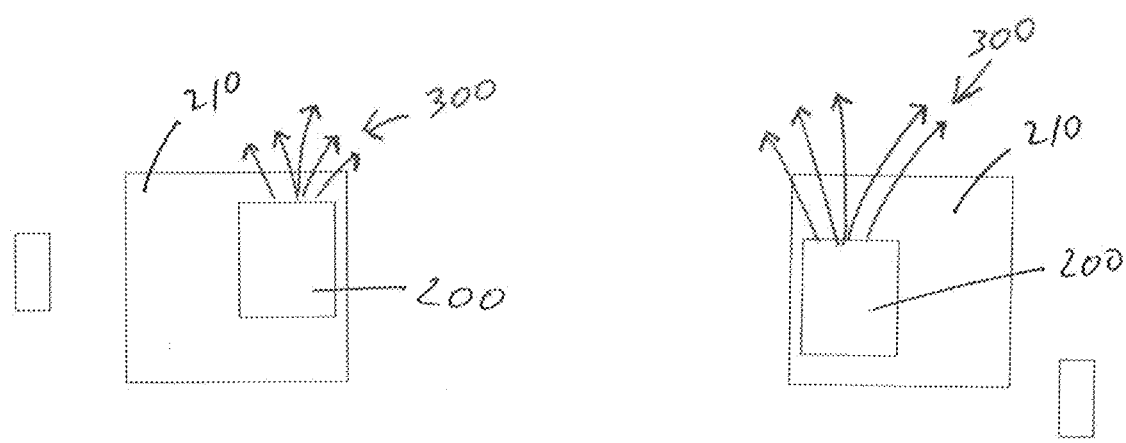
Figure 8:
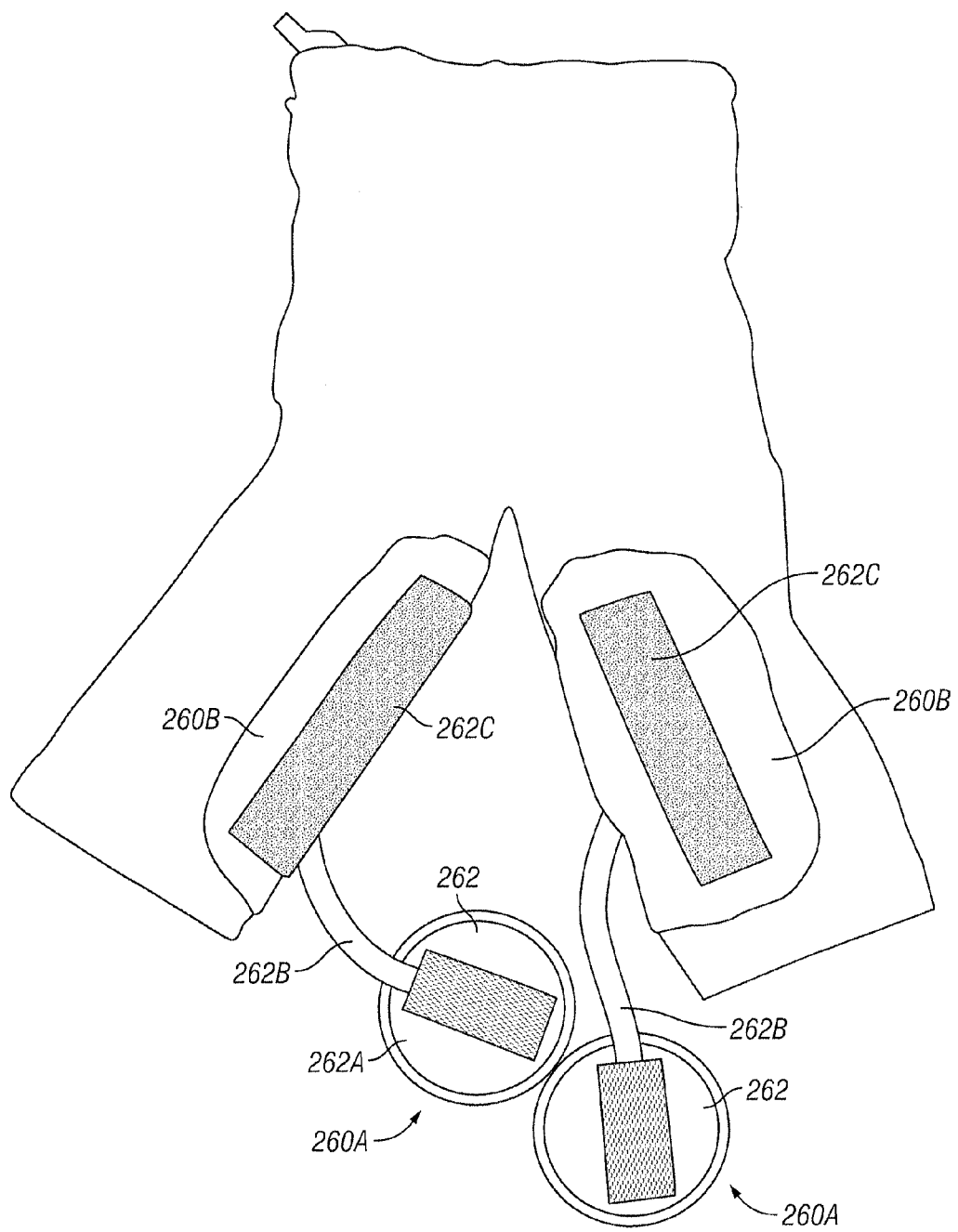
FIG. 8 is a plan view of an apparatus for discouraging W-sitting according to another embodiment of the present invention.
Figure 9:
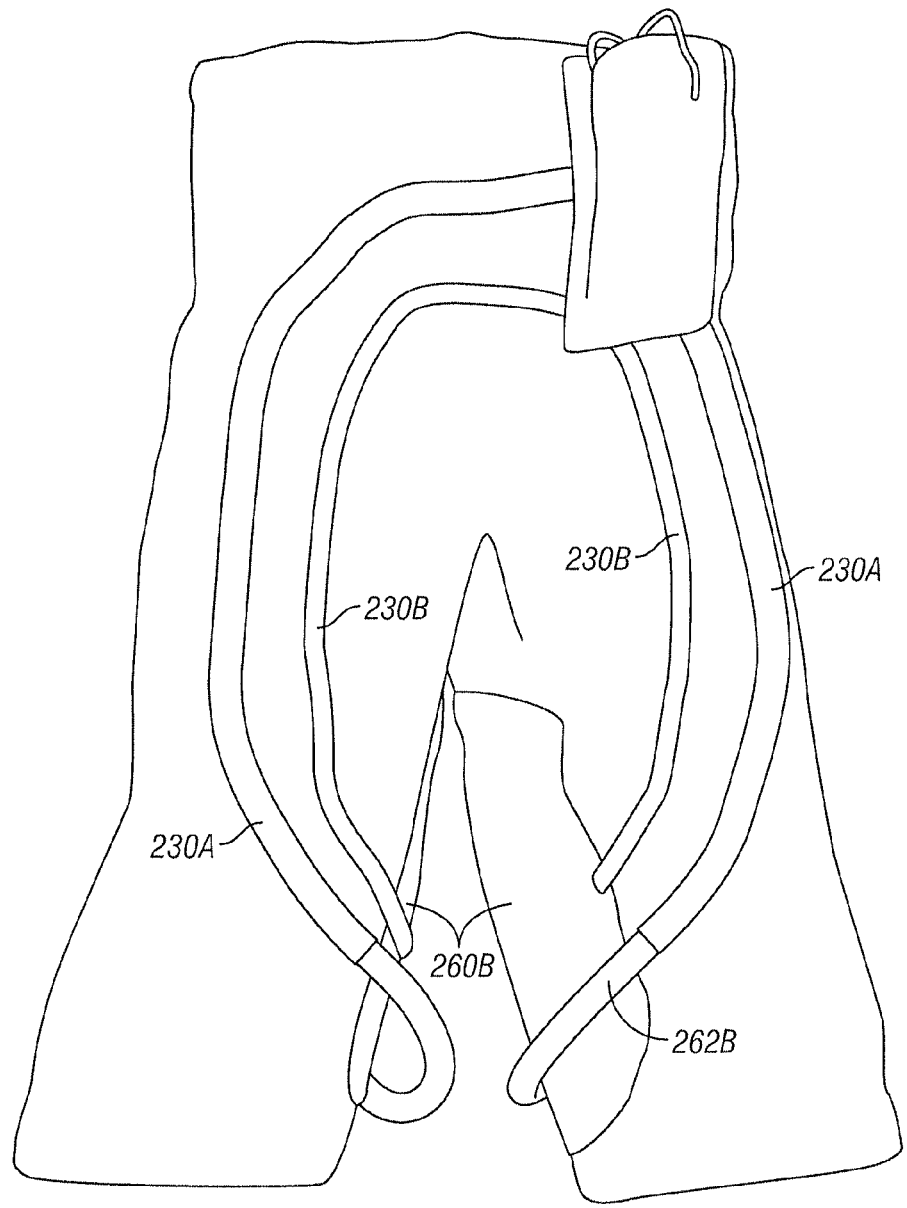
FIG. 9 is a plan view of the apparatus of FIG. 8 from the opposite side.
Figure 10:
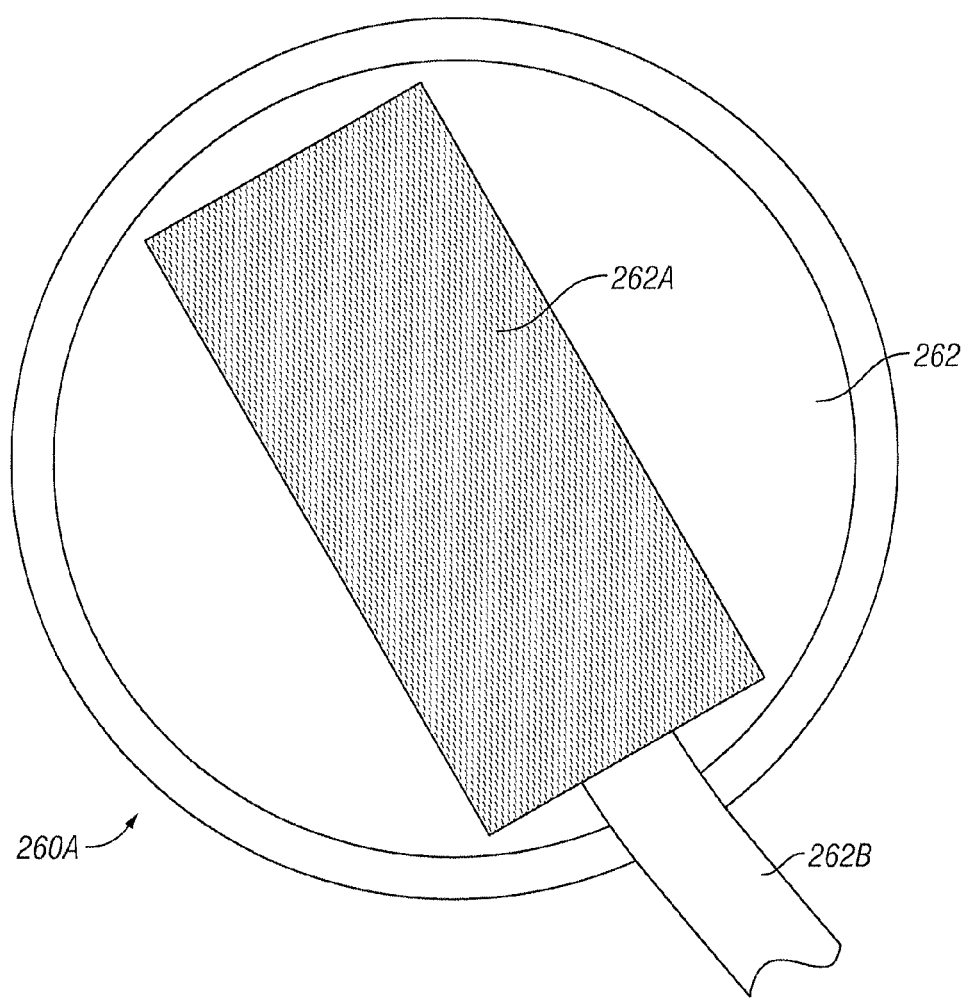
FIG. 10 is a plan view a first portion of a switch that is a component of the apparatus shown in FIG. 8.

FIG. 7 is a schematic view of another embodiment of an apparatus for discouraging W-sitting according to the present invention. In this embodiment, wireless components have been substituted for the various conductors and wires of the previous embodiments. A transmitter 200 is associated with or incorporated into each switch 210 and a receiver 220 is associated with or incorporated into indicator 230. Power sources 240 are associated with or incorporated into each transmitter 200 and indicator 230. Triggering switches 210 wirelessly transmits a signal 300 from transmitters 200 to receiver 220, thereby activating indicator 230. Note that in this embodiment, it is not necessary to attach the indicator, receiver and associated power source to the patient. They simply need to be in close enough proximity to receive the signal from the transmitters and for the patient or caregiver to sense the indicator when it is activated.

In another alternative embodiment, the power supply and indicator could be incorporated into or placed on a belt or other strap, sleeve or similar device and positioned about a patients waist, arm or other body location. The switches could be placed on belts, straps, sleeves or similar type devices such that they could be positioned over a patient's garment or directly on the knees. In such an embodiment, either wired or wireless technology could be utilized. This embodiment of the invention would permit the apparatus to be utilized with various articles of clothing owned by the patient such that treatment is not limited to the time during which the patient is wearing a specific garment into which the switches, power source and indicator are integrated.

FIGS. 8-11 illustrate an apparatus for discouraging W-sitting according to another embodiment of the present invention. In this embodiment, first portions 260A of switches 260 are foam or other flexible members having a first side 261 and a second side 262 covered with or constructed from a conductive material, such as the conductive fabric used for conductors 30. One portion of a fastening means, such as hook portion 262A of a hook and loop type fastening system, is connected to side 262 by adhesive, stitching or other means. A nonconductive sheath 262B having conductive material (such as that used for conductors 30) enclosed therein extends from side 262. The conductive fabric extends from the end of sheath 262B and is in electrical contact with the conductive side 262 of switch portion 260A. At the opposite end of sheath 262B (FIG. 9), the conductive fabric is in electrical contact with a conductor 230A. Switches 260 further include a second portion 260B in the form of a conductors stitched, adhered or otherwise secured to the legs of the garment. Portions 260B can also be integrally formed parts of the garment. Each portion 260B is in electrical contact with a conductor 230B. In the embodiment shown, portions 260B are patches of conductive fabric. The second portion of the fastening means, such as, loop portion 262C of a hook and loop type fastening system, is secured to second portions 260B of switches 260 as shown.

Figure 11:
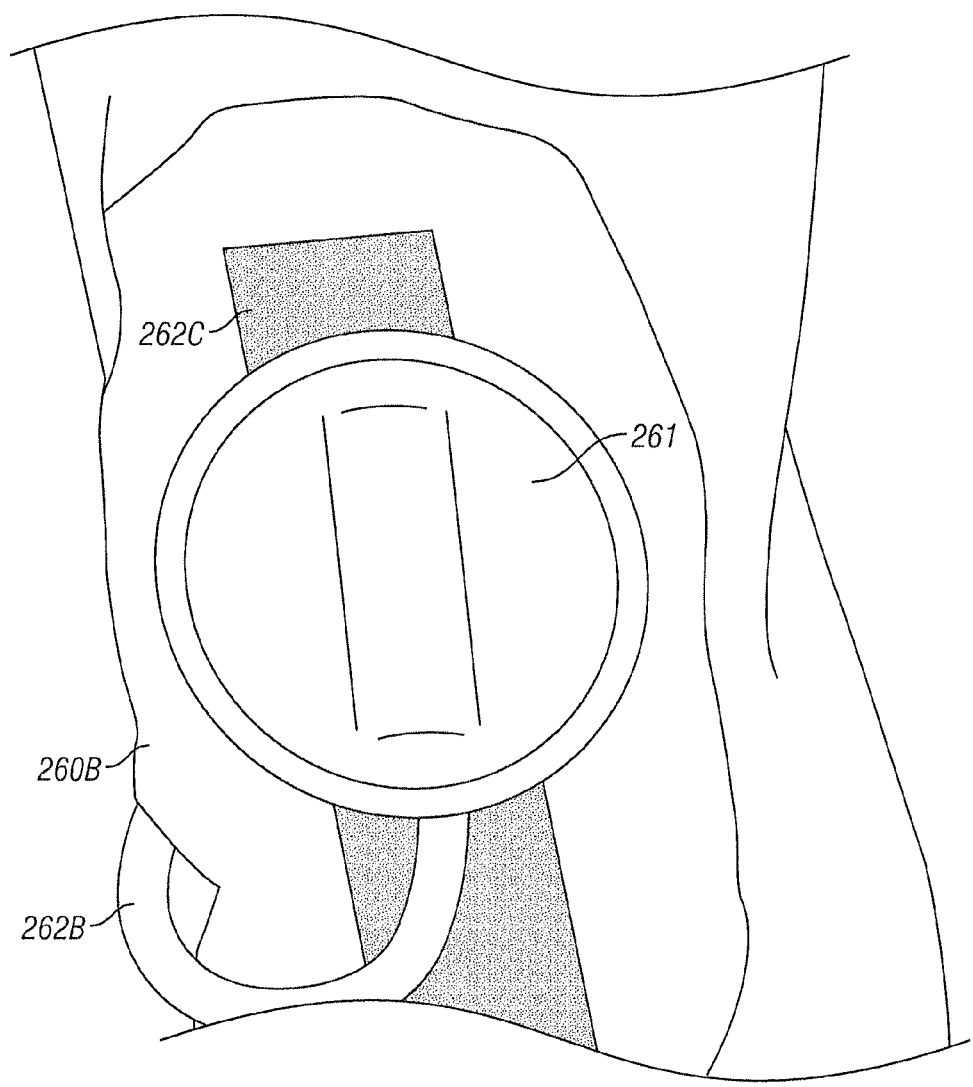
FIG. 11 is a plan view showing the switch portion of FIG. 10 positioned on the apparatus of FIG. 8.

In use, switch portions 260A are secured to the garment by fastening means 262A/262C as shown in FIG. 11. In this position, conductive side 262 of switch portion 260A is elevated above switch portions 260B. However, when the wearer assumes a W-sitting position, switch portions 260A will tilt and/or compress, thereby placing conductive side 262 in contact with portions 260B and completing the circuit. Upon completion of the circuit, an audio or other sensory signal is produced to alert the wearer to switch positions.

Although the present invention has been shown and described in detail the same is to be taken by way of example only and not by way of limitation. Numerous changes can be made to the embodiments shown without departing from the scope of the invention. For example, indicator 50 does not have to emit a sound. A light or other visual indicator could be used. The indicator could also vibrate. Indicator 60 and switches 60 can plug into a socket or other holder that is electrically coupled to conductors 30. In this manner, the indicator that works most effectively for a given child can be utilized. Furthermore, switches 60 can be selected that best correspond to a particular patient's weight, knee configuration and W-sitting position. The present invention may be further modified within the spirit and scope of this disclosure. The application is, therefore, intended to cover any variations, uses, or adaptations of the invention using its general principles. Further, this application is intended to cover such departures from the present disclosure as come within known or customary practice in the art to which this invention pertains.

I claim:

1. An orthotic apparatus including:
   a garment;
   a first switch connected to the garment;
   a second switch connected to the garment;
   a power source connected to the garment;
   an indicator connected to the garment, the indicator activating only when both switches are activated during the same time period;
   a first electrical conductor electrically coupled to the first switch and the power source;
   a second electrical conductor electrically coupled to the power source and the indicator;
   a third electrical conductor electrically coupled to the indicator and the second switch;
   a fourth electrical conductor electrically coupled to the first switch and the second switch; and
   wherein the first and second switches are positioned so as to activate only when a person wearing the garment assumes a W-sitting position.

2. The orthotic apparatus according to claim 1, wherein the indicator produces an audible sound.

3. The orthotic apparatus according to claim 1, wherein the indicator produces a visible signal.

4. The orthotic apparatus according to claim 1, wherein at least one of the conductors is a piece of conductive cloth.

5. The orthotic apparatus according to claim 1, wherein the garment is made from a stretchable fabric material.

6. The orthotic apparatus according to claim 1, wherein the power source and indicator are located in a housing.

7. The orthotic apparatus according to claim 1, wherein at least one of the switches is removably connected to the garment so as to be movable from a first location on the garment to a second location on the garment.

8. An orthotic apparatus including:
a first switch;
a second switch;
a power source;
a wireless transmitter and a wireless receiver;
means for selectively positioning the first and second switches on a person;
an indicator that activates only when the first and second switches are activated during the same time period; and
wherein the first and second switches are activated only when the person assumes a W-sitting position and activating the first and second switches causes the transmitter to send a signal to the receiver, which in turn activates the indicator.

9. The orthotic apparatus according to claim 8, further including a plurality of conductors electrically coupling the first switch, second switch, power source and indicator in an electric circuit.

10. The orthotic apparatus according to claim 8, further including a garment.

11. The orthotic apparatus according to claim 8, wherein the means includes a strap.

12. The orthotic apparatus according to claim 8, wherein the means includes a sleeve.

13. The orthotic apparatus according to claim 8, further including means for connecting the indicator to a person.

14. The orthotic apparatus according to claim 13, wherein the means includes a strap.

15. The orthotic apparatus according to claim 13, wherein the means includes a sleeve.

16. The orthotic apparatus according to claim 8, wherein the means includes a garment.

17. The orthotic apparatus according to claim 16, wherein the means includes a hook and loop fastening system.

* * * * *